United States Patent [19]

Cory

[11] Patent Number: 5,560,372
[45] Date of Patent: Oct. 1, 1996

[54] NON-INVASIVE, PERIPHERAL NERVE MAPPING DEVICE AND METHOD OF USE

[76] Inventor: Philip C. Cory, 300 N. Willson, Suite 303C, Bozeman, Mont. 59715

[21] Appl. No.: 190,394

[22] Filed: Feb. 2, 1994

[51] Int. Cl.⁶ ..................................................... A61B 5/05
[52] U.S. Cl. ........................................... 128/741; 128/734
[58] Field of Search ..................................... 128/639, 644, 128/734, 741, 774

[56] References Cited

U.S. PATENT DOCUMENTS

| | | | |
|---|---|---|---|
| 4,557,271 | 12/1985 | Stoller et al. | 128/734 |
| 5,092,344 | 3/1992 | Lee | 128/741 |
| 5,215,100 | 6/1993 | Spitz et al. | 128/741 |
| 5,284,153 | 2/1994 | Raymond et al. | 128/741 |
| 5,311,878 | 5/1994 | Brown et al. | 128/734 |
| 5,313,956 | 5/1994 | Knuttson et al. | 128/741 |
| 5,327,902 | 7/1994 | Lemmen | 128/734 |
| 5,348,006 | 9/1994 | Tucker | 128/639 |

*Primary Examiner*—Angela D. Sykes
*Attorney, Agent, or Firm*—Lowe, Price, LeBlanc & Becker

[57] ABSTRACT

A device for non-invasively locating the presence of peripheral nerves. The peripheral nerve mapping device has a sampling electrode comprising an array of a plurality of sub-electrodes, a reference electrode, a square wave constant current source, and a multiplexer serially multiplexed to the array of the sub-electrodes. The voltage differential between each of the sub-electrodes and the reference electrode is measured as the current is serially distributed to the sub-electrodes and displayed on an array of light emitting diodes. The voltage differential indicates the presence of peripheral nerves and may be used to identify sites of nerve trauma or transection.

13 Claims, 5 Drawing Sheets

NON-INVASIVE, PERIPHERAL NERVE MAPPING DEVICE AND METHOD OF USE

TECHNICAL FIELD

This invention relates to a non-invasive, peripheral nerve mapping device for locating transcutaneous nerves and a method for its use. In particular, this invention relates to a non-invasive, peripheral nerve mapping device comprising a sampling electrode having an array of a plurality of sub-electrodes, a reference electrode, a square wave constant current source, and a multiplexer. The constant current output is serially multiplexed to the array of sub-electrodes, while the voltage differential between each of the sub-electrodes and the reference electrode is measured as the current is serially distributed to the array of sub-electrodes. Variation in the voltage difference between electrodes indicates the presence of peripheral nerves. Further, this invention relates to a method of identifying peripheral nerve activity by applying a sampling electrode having a multiplicity of electrodes to the epidermal surface of a patient and analyzing the output voltage of the sub-electrodes.

BACKGROUND OF THE INVENTION

Variations in the electrical conductance of the intact skin of human beings has been recognized for many years. Particularly high conductance sites have been associated with acupuncture points as well as with trigger points in myofascial pain syndromes. However, the realization that this change in electrical skin conductance was related to the presence of subcutaneous nerves was only made recently by the inventor, and represents a unique finding. Although the measurement of transcutaneous: electrical conductivity has been used for other purposes, it has never before been shown to reveal the position of neural tissue.

The present non-invasive-peripheral nerve mapping device and method may be used to indicate the site of nerve injury or nerve transection. Sudden loss of transcutaneous electrical hyperconductivity along the course of a peripheral nerve is indicative of interruption of the nerve fiber whereas a focal increase in the transcutaneous electrical hyperconductivity along the course of a peripheral nerve is evidence of a site of nerve injury without actual transection.

SUMMARY OF THE INVENTION

It is an object of the present invention to provide a device which can non-invasively locate peripheral nerves.

It is a further object of the present invention to provide a method for identifying abnormal peripheral nerve activity secondary to injury.

In accordance with these and other objects of the invention, the present invention provides a device which can non-invasively map peripheral nerves comprising:

means for sampling a plurality of electrical conductance sites;

reference electrode means; and means for supplying a constant current source.

More preferably the present invention provides a device which can non-invasively map peripheral nerves comprising:

a sampling electrode comprising an array of a plurality of sub-electrodes;

a reference electrode;

a constant current source; and a multiplexer having an output, said multiplexer output being serially multiplexed to said array of plurality of sub-electrodes;

wherein said constant current output is serially multiplexed by said multiplexer to said array of plurality of sub-electrodes, the voltage differential between each of the, sub-electrodes and the reference electrode being measured as the current is serially distributed to said array of plurality of sub-electrodes, said voltage differential indicating the presence of peripheral nerves. The square wave, constant current source is preferably provided with an adjustable frequency output and an adjustable amplitude output.

Further, in accordance with these and other objects of the invention, the present invention provides a method for non-invasively identifying peripheral nerve activity comprising the, steps of:

applying means for sampling a plurality of electrical conductance sites to the epidermal surface of a patient;

applying reference electrode means to the epidermal surface of the patient;

applying a constant current through said sampling means;

and analyzing the voltage output of said sampling means.

More preferably, the present invention provides a method for non-invasively identifying peripheral nerve activity comprising the steps of:

applying a sampling electrode to the epidermal surface of a patient, said sampling electrode comprising an array of a plurality of sub-electrodes;

applying a reference electrode to the epidermal surface of said patient;

applying a constant current through said sub-electrodes; and analyzing the output voltage of said sub-electrodes.

BRIEF DESCRIPTION OF THE DRAWINGS

The invention will hereinafter be further described with reference to the enclosed drawings.

DETAILED DESCRIPTION OF THE INVENTION

Figure 1A:
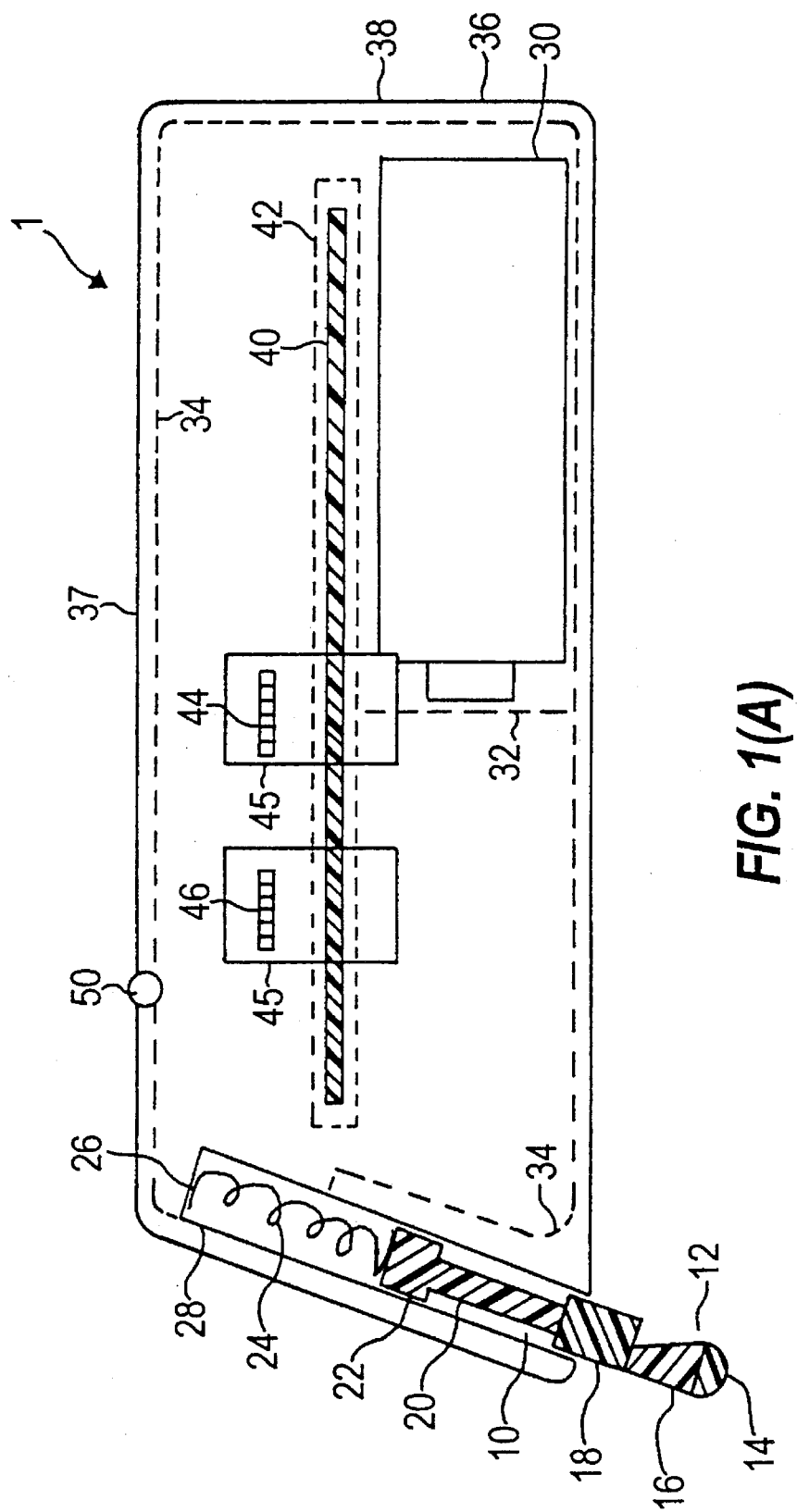
FIG. 1(A) shows a cross-sectional side view of the nerve mapping device according to the invention.

The essential characteristics of the measurement device of this invention are that a constant current is applied between the sampling electrodes and reference electrode on the epidermal surface. The voltage difference between the two electrodes is measured and varies from adjacent skin sites as the electrical conductance of the skin changes. Hence, decreases in the voltage at constant current is a direct measure of increased skin electrical conductance.

Recognition that human skin is not a uniform surface is essential in the design of this system. Attempts to measure skin conductance with a metal electrode universally meet with failure due to the presence of preferential conductance pathways down sweat glands, the development of back EMF (ElectroMotive Force) and the formation of thin, oxidation films on the metal surface. It has been discovered that this effect can be obviated by use of an electrode system which employs an aqueous interface between the skin surface and the electrode, producing very stable, reproducible readings over time. The aqueous electrode preferably has a tip comprising an absorbent material such as an open-cell sponge or felt and is resiliently responsive to pressure and the release thereof. Thus, the electrode can be moved over body surface terrain easily and maintain electrical contact.

According to the present invention, a non-invasive peripheral nerve mapping device is provided comprising: means for sampling a plurality of electrical conductance sites; reference electrode means; and means for supplying a constant current source. The sampling means may comprise a sampling electrode having an array of a plurality of sub-electrodes. The device may further comprise means for multiplexing the current, the multiplexer means having an output and being serially multiplexed to the array of plurality of sub-electrodes. The voltage differential between each of the sub-electrodes and the reference electrode is measured as the current is serially distributed to the sub-electrodes. The voltage differential indicates the presence of peripheral nerves.

A preferred embodiment according to the present invention is a non-invasive peripheral nerve mapping device comprising:

a sampling electrode comprising an array of a plurality of sub-electrodes;

a reference electrode;

a constant current source; and a multiplexer having an output, said multiplexer output being serially multiplexed to said array of plurality of sub-electrodes;

wherein said constant current output is serially multiplexed by said multiplexer to said array of plurality of sub-electrodes, the voltage differential between each of the sub-electrodes and the reference electrode being measured as the current is serially distributed to said array of plurality of sub-electrodes, said voltage differential indicating the presence of peripheral nerves.

Typically, the constant current source means is provided with means for adjusting frequency output and means for adjusting current output. The amplitude may be adjustable from 0.0 to 1.0 milliamps, and the frequency may be adjustable from 0 to 1000 hertz. The constant current source means may comprise a battery such as nine-volt battery or may be any other current source.

Means for adjusting current are known in the art. Current amplitude may be controlled by means of a finger-tip wheel control and frequency can be adjusted from 0–1000 hertz by thumb wheel controls. A single frequency adjustment means may be employed, but typically, for fine adjustment, several adjustment means are used such as a first frequency adjustment means for ON/OFF and coarse-gain adjustments and a second or fine-gain adjustment. A third ultra-fine-gain adjustment means may be added when necessary. The constant current output is serially multiplexed to an array of sub-electrodes.

The peripheral nerve mapping device preferably further comprises light emitting diodes means, for example, LEDS, wherein the largest voltage differential between the sub-electrodes and said reference electrode is measured as the current is serially distributed to the array of sub-electrodes. The voltage differential may be displayed as an illuminated LED among the array of LEDS, which indicate the sub-electrode measuring the greatest voltage differential.

The means for sampling a plurality of electrical conductance sites preferably comprises an sampling electrode having an array of plurality of sub-electrodes. Each plurality of sub-electrodes is provided with means for providing an aqueous interface means. The aqueous interface means may comprise an absorbent tip which is capable of holding an aqueous solution or gel. The absorbent tip may be made of felt, an open-celled sponge or any other element capable of maintaining an aqueous interface. It is preferred that each absorbent tip of each sub-electrode have a surface area which is approximately 3–20 square millimeters.

The device preferably comprises guide tube means mounted thereon. This may be a stainless steel cylinder having both ends open—the first end providing an outlet for a movable piston and the other permitting wiring to the multiplexer. Accordingly, the sub-electrodes may be mounted on movable pistons, each piston being provided with a guide tube which may be stainless steel and are movable through the guide tubes. The pistons preferably comprises a spring means mounted in the end of each guide tube to control the movement is the pistons in response to external pressure and the release thereof.

The reference electrode means used in this invention may be a standard silver-silver chloride electrode as used for electrocardiographic studies or monitoring. However, it is under,stood that any reference electrode may be used which will perform in accordance with the objectives of this invention. A conductive, metal bar held in the hand of the study subject or a carbon-impregnated silastic pad provided with a layer of pharmaceutical electrode gel placed on the bottom of the pad and positioned against the skin are other suitable systems.

Figure 2:
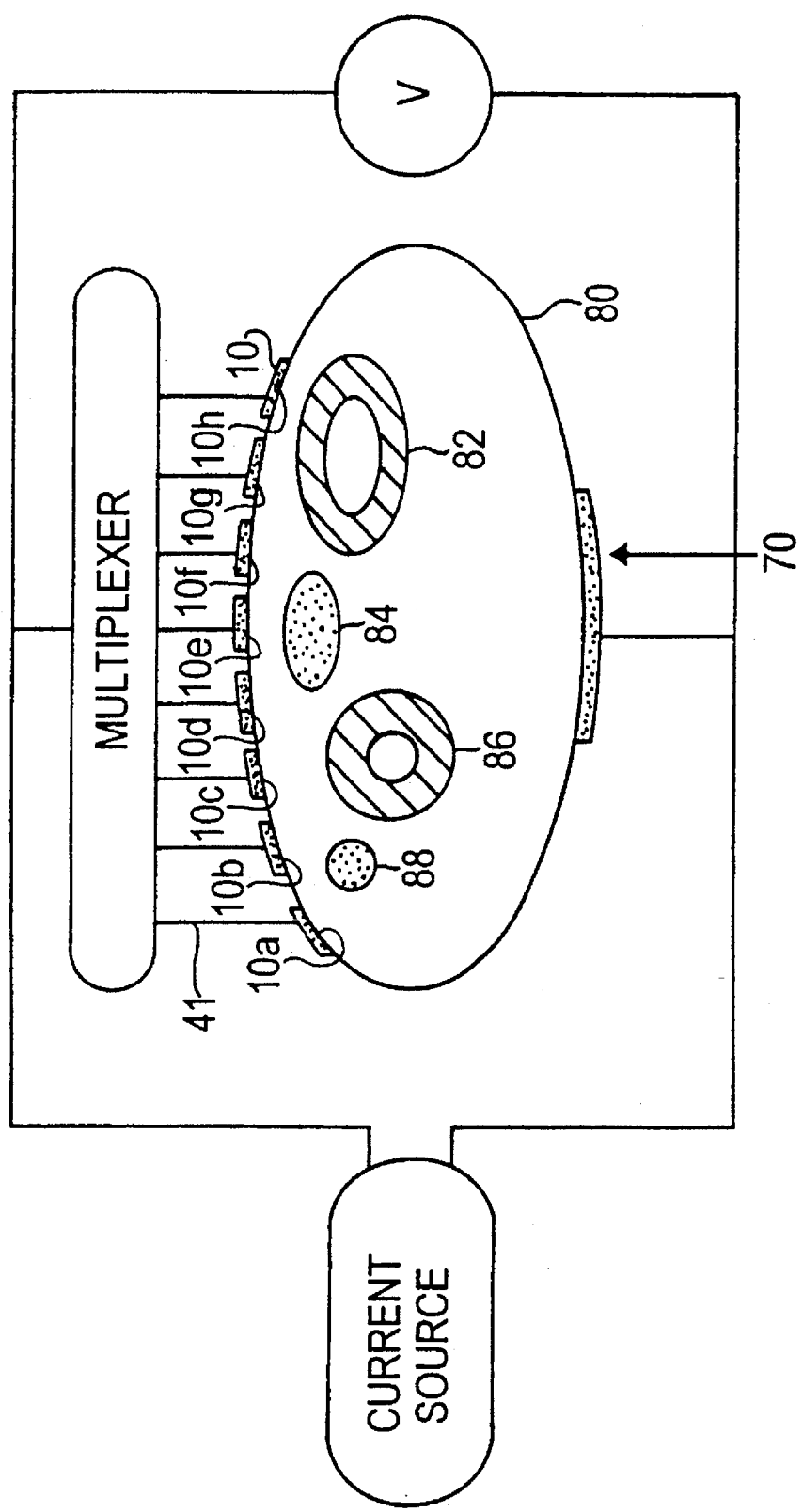
FIG. 2 is a circuit diagram of the peripheral nerve mapping device.

Any number of t:he sub-electrode means may be used, however, it is preferred that at least two sub-electrodes be arranged in a linear array, and more preferably, eight sub-electrodes may be placed in a linear array as shown in FIG. 2. The sub-electrodes may be positioned in a matrix array in any pattern or number and the size and shape of each sub-electrode may individually vary.

The present invention is also related to a method of utilizing the peripheral nerve mapping device to identify peripheral nerve activity comprising the steps of: applying means for sampling a plurality of electrical conductance sites to the epidermal surface of a patient; applying reference electrode means to the epidermal surface of the patient; applying a constant current through said sampling means; and analyzing the voltage output of the sub-electrodes. The sampling means may comprise sampling electrode means having an array of a plurality of sub-electrodes.

More preferably, a method of utilizing the peripheral nerve mapping device to identify peripheral nerve activity is provided comprising the steps of:

applying the sampling electrode to the epidermal surface of a patient, the sampling electrode comprising an array of a plurality of sub-electrodes;

applying a reference electrode to the epidermal surface of the patient;

applying a constant current through the sub-electrodes; and analyzing the output voltage of the sub-electrodes.

The output voltage is analyzed for decreased voltages and indicates the presence of peripheral nerves. Preferably, the current output is serially multiplexed by a multiplexer means to an array of a plurality of sub-electrodes, the voltage differential between each of the sub-electrodes and the reference electrode being measured as the current is serially distributed to the array of plurality of sub-electrodes. Preferably, the current is displayed as an illuminated LED among the array of LEDS indicative of the sub-electrode measuring the greatest voltage differential.

The method of the present invention provides a means for indicating the point of trauma for injured peripheral nerves. Thus, the activity, or lack thereof, of nerves injured by direct trauma or stretch may be diagnosed without using invasive, painful techniques to explore and locate sites of trauma.

With respect to the Figures, the peripheral nerve mapping device (1) as shown in FIG. 1(A) comprises means for sampling a plurality of electrical conductance sites having a plurality of at least two sub-electrodes (10a–h) having a probe tip (12). Probe tip (12) comprises means for providing an aqueous interface (14) which may be a cup-shaped molded metal tip covered with felt as shown in the figure or other absorbent material. The cup-shaped molded metal tip (not-shown) may be metal foil which is laminated to the felt. Probe tip (12) is preferably provided with connector (16) to secure the aqueous interface (14) to the sampling electrode (10). The connector may comprise any shape and may be removable in order to replace aqueous interface (14).

Probe tip (12) moves through guide tube (28) which may be stainless steel and is provided with piston guide (18) to align sliding within the stainless steel guide tube (28). Piston guide (18) is attached to piston (20), connected to piston spring stop (22). A spring (24) is provided between piston spring stop (22) and end spring stop (26) to permit the piston (12) to be variably moved through tube (28) in response to pressure exerted on aqueous interface (14).

Guide tube (28) is mounted on enclosure (36) having a top (37) and end (38). Enclosure (36) may be provided with interior grooves (34) for holding stainless steel guide tube (28) and which may be made of plastic or other suitable material.

Nerve mapping device (1) is provided with a circuit board (40) which may be rested on circuit board-holding grooves (42). Leads 41 from circuit board (40) may be routed through a hole (not shown) in end spring stop (26) and a bore (not shogun) through piston (20) to aqueous interface (14). Frequency control means comprise thumb wheel controls (44) and (46) are preferably provided on the left side of enclosure (36) for easy access. Thumb wheel control (46) functions as the ON/OFF switch and the coarse-gain control. Thumb wheel control (44) functions as the fine-gain control. Amplitude control means comprising finger-tip wheel control (48) as shown in FIG. 2 functions as the current amplitude adjuster. A plurality of amplitude controls means for enhanced amplitude adjustment is contemplated. Preferably, the nerve mapping device is provided with variable intensity light (50) having a light intensity proportional to the current in the corresponding sub-electrodes (10a–h).

Figure 1B:
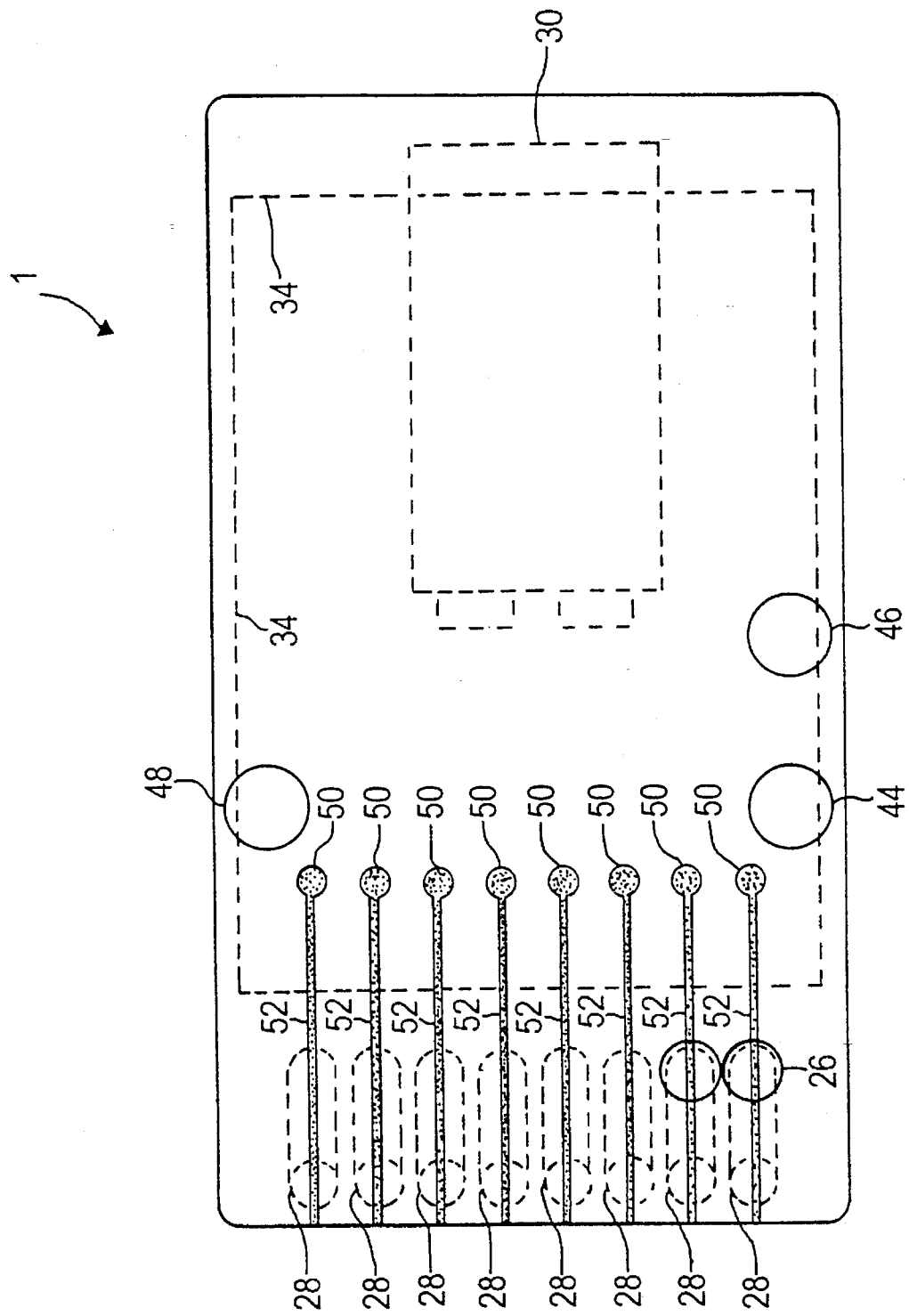
FIG. 1(B) is a top view of the nerve mapping device.

FIG. 1(B) depicts a top view of the nerve mapping device (1). Indicator grooves (52) on top of enclosure (36) extend to variable intensity lights (50) to visually match each sub-electrode (10a–h) to the corresponding light (50). Finger-tip wheel control (48) is shown on the left side of the device and thumb wheel controls (44) and (46) are shown the on right.

Figure 1C:
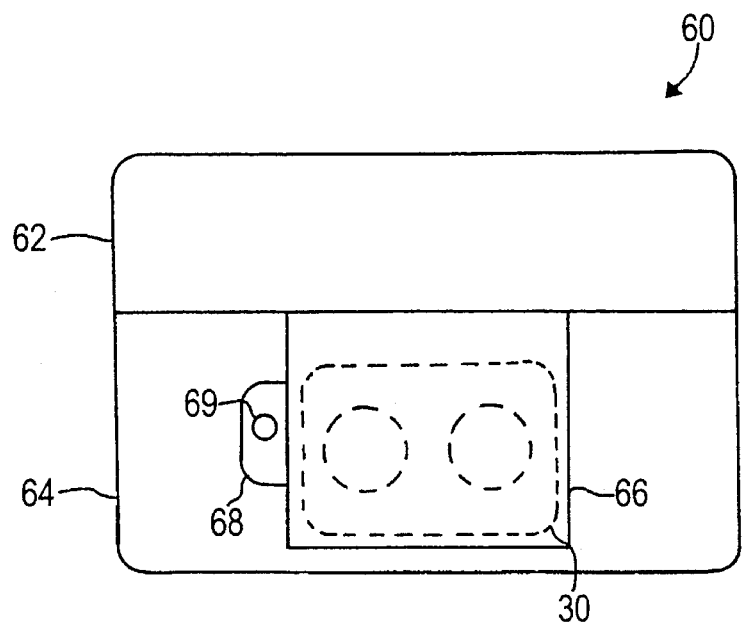
FIG. 1(C) is a back view of the nerve mapping device.
Figure 1D:
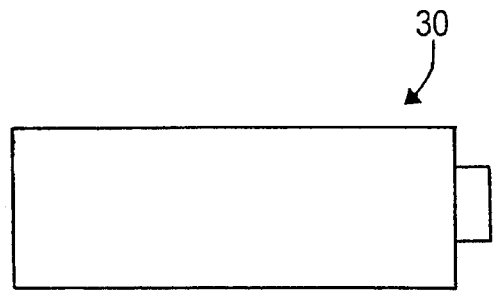
FIG. 1(D) is a side view of a battery.
Figure 1E:
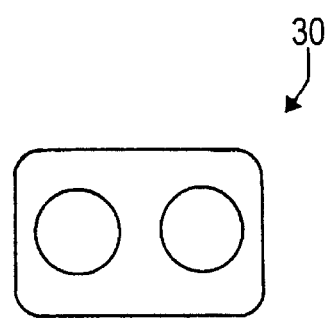
FIG. 1(E) is a front view of a battery.

FIG. 1(C) depicts a back view of the peripheral nerve mapping device. Enclosure (36) is provided with battery door (66) having door tab (68) and screw hole (69). The nerve mapping device may be manufactured in two piece comprising upper half (62) and lower half (64) which may be glued together after the interior components are assembled. FIG. 1(D) depicts a side view of battery (30) which is preferably a nine-volt battery. FIG. 1(E) depicts a front view of battery (30).

FIG. 2 is a circuit diagram of the non-invasive, peripheral nerve mapping device according to the present invention as it is positioned over the forearm of a patient. The sampling electrode (10) depicted herein comprises eight sub-electrodes (10a–h) having leads (41) arranged in a linear array and applied to the volar surface of the forearm on the epidermal surface (80). The reference electrode (70) is placed on the dorsal forearm. A constant current output is applied between the two electrodes (10, 70) on the epidermal surface (80). The voltage difference V between the two electrodes is measured and varies from adjacent skin sites as the electrical conductance of the skin changes.

FIG. 2 illustrates one embodiment of the reference electrode. However, it is understood that any reference electrode may be used which will perform in accordance with the objectives of this invention. The reference electrode (70) may comprise a conductive carbon impregnated silastic pad provided with an insulated metal foil sheet laminated thereto. The metal foil sheet is in electrical contact with a connector element. The reference electrode may further contain adhesive layer laminated to the bottom of the silastic pad provided with a silicon release sheet attached to the adhesive layer. Reference electrode may comprise a carbon-impregnated silastic pad provided with a layer of pharmaceutical electrode gel placed on the bottom of the pad to be positioned against the skin.

Figure 3A:
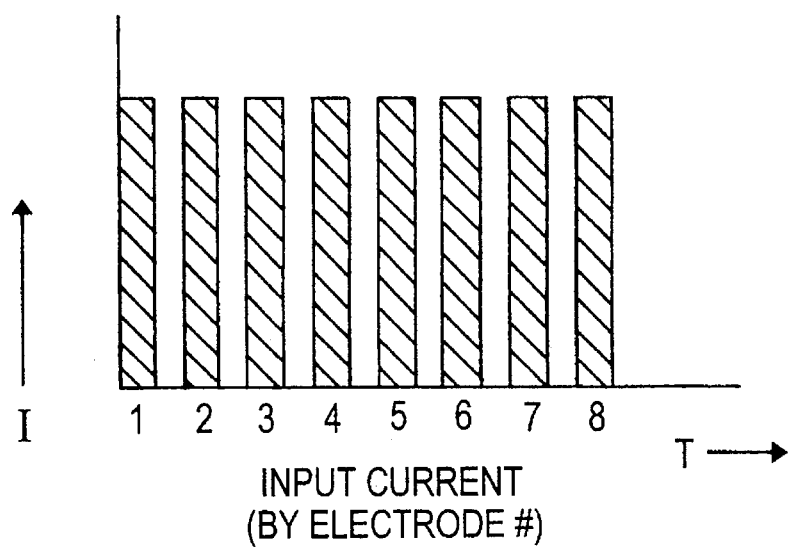
FIG. 3(A) graphically depicts individual sub-electrode input current amplitude.
Figure 3B:
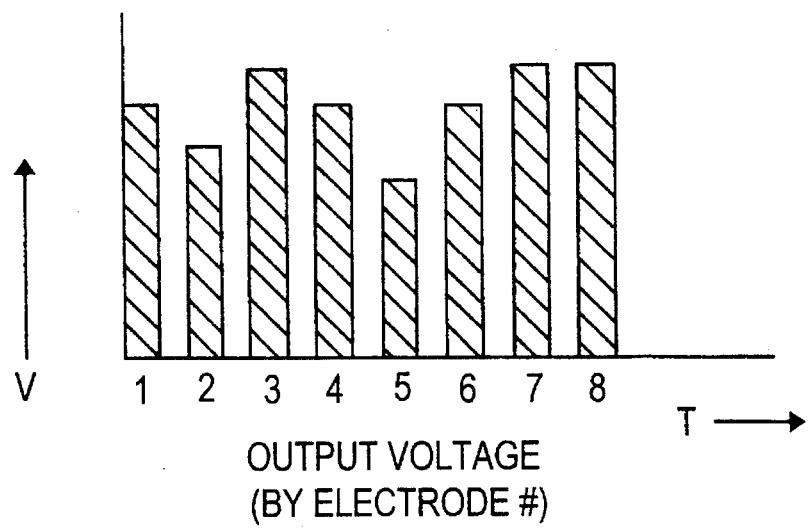
FIG. 3(*b*) is a graphic display of the voltage output by electrode number.

FIG. 3(A) depicts the constant current input (I) for each sub-electrode (10a through 10h), numbers 1–8 respectively, as shown in FIG. 2. FIG. 3(B) depicts the voltage output V for each sub-electrode.

With reference to FIG. 2 and FIG. 3(B), sub-electrode number (10b), number 2 in FIG. 3(B) is positioned over ulnar nerve (88). As shown in FIG. 3(B), sub-electrode (10b) indicates the position of the ulnar nerve (88) by a decrease in output voltage. Similarly, reference sub-electrodes (10d) and (10e), numbers 4 and 5 in FIG. 3(B), display a similar output voltage decrease as they are positioned over median nerve (84). Thus, the non-invasive, peripheral nerve mapping device according to the present invention accurately identifies the location of subcutaneous nerves. Voltage minima (conductance maxima) are observed over the ulnar and median nerves (88, 84) at constant current. Sites of decreased skin voltage differentials are mapped and have been shown by nerve stimulator technique, direct dissection and local anesthetic blockage, in animal and human models, to correspond to the location of subcutaneous nerves.

Other uses and modifications of the present invention are obvious to one of ordinary skill in the art and within the scope of the invention.

I claim:

1. A non-invasive, peripheral nerve mapping device comprising:

means for sampling a plurality of electrical conductance sites, said sampling means comprising a sampling electrode having an array of a plurality of sub-electrodes, each sub-electrode comprising an absorbent tip having a surface area of approximately 3–20 square millimeters, each sub-electrode being mounted on movable pistons;

guide tube means mounted to said device, said pistons being movable through said guide tube means, each of said sampling electrodes being in electrical contact with each of said guide tube means;

reference electrode means comprising a standard silver-silver chloride electrocardiographic electrode;

a square wave constant current source with an adjustable frequency output and an adjustable amplitude output;

a multiplexer having an output, said multiplexer output being serially multiplexed to said array of plurality of sub-electrodes;

an array of light emitting diodes to display conductivity measurements;

wherein a current from said constant current source is selectively conveyed by said multiplexer to said sub-electrodes across the skin of a patient, with a corresponding voltage difference between each of the sub-electrodes and the reference electrode being measured as the current is conveyed to said sub-electrodes and displayed by said array of light emitting diodes, the displayed voltage difference being indicative of a local electrical conductance of said intact skin.

2. The device according to claim 1, wherein the current is adjustable from 0.0 to 1.0 milliamps, and the frequency is adjustable from 0 to 1000 hertz.

3. The non-invasive, peripheral nerve mapping device according to claim 1, wherein the array of electrodes is a linear array of eight electrodes.

4. A method of non-invasively locating peripheral nerves in a patient's body, comprising the steps of:

a) providing a nerve mapping device having
   i) a plurality of sub-electrodes;
   ii) a reference electrode; and
   iii) a source of constant current that can be directed to each of said sub-electrodes;

b) placing said sub-electrodes and said reference electrode in contact with a patient's skin;

c) supplying said constant current to each of said sub-electrodes;

d) measuring a respective local voltage difference between each of said sub-electrodes and said reference electrode across said skin of said patient, said local measured voltage difference corresponding to a local electrical conductance of said skin of said patient; and e) comparing said respective local measured voltage differences for said sub-electrodes; and thereby identifying a presence of a peripheral nerve based on a decrease in measured local voltage for one of said sub-electrodes relative to the measured local voltage differences for other sub-electrodes.

5. The method of claim 4 comprising the step of multiplexing said constant current serially to said sub-electrodes.

6. The method of claim 4, wherein said constant current is adjustable in frequency and amplitude.

7. The method of claim 4 further comprising the step indicating which said sub-electrode represents said decrease in measured voltage.

8. The method of claim 4 wherein said placing step further comprises placing each sub-electrode and said reference electrode in opposing relationship on said patient's skin.

9. A non-invasive nerve mapping device, comprising:

a) a housing;

b) a plurality of sub-electrodes, at least a portion of each sub-electrode being arranged in said housing:

c) a square wave constant current source;

d) a multiplexer in said housing, said multiplexer providing said constant current serially to each of said sub-electrodes;

e) a reference electrode;

f) a voltage measuring device for measuring a respective voltage difference between each of said sub-electrodes and said reference electrode and between said sub-electrodes when said constant current is applied to each said sub-electrode, the voltage difference indicating electrical conductance of said intact skin; and g) an indicator for each sub-electrode, each indicator being responsive to a decrease in voltage as measured by said voltage measuring device, whereby a peripheral nerve presence is determined adjacent a sub-electrode associated with said decrease.

10. The device of claim 9 wherein each said indicator is a light emitting diode.

11. The device of claim 9 wherein said reference electrode is one of a conductive carbon impregnated silastic pad with an insulated metal foil sheet laminated thereto and a silver-silver chloride electrode.

12. The device of claim 9 further comprising adjustable frequency and amplitude circuits for said constant current source.

13. The device of claim 9 wherein said sub-electrodes further comprises a linear array of eight electrodes.

* * * * *